United States Patent
Petro et al.

(10) Patent No.: US 6,726,843 B2
(45) Date of Patent: Apr. 27, 2004

(54) INVERSE CHROMATOGRAPHY METHODS AND APPARATUS FOR EVALUATION OF INTERACTIONS BETWEEN MODIFYING AGENTS AND RECEPTORS COMPRISING NATURAL OR ARTIFICIAL MAMMALIAN TISSUE

(75) Inventors: Miroslav Petro, San Jose, CA (US); Ralph B. Nielsen, San Jose, CA (US); Jacqueline M. Regan, Santa Clara, CA (US)

(73) Assignee: Symyx Technologies Inc., Santa Clara, CA (US)

( * ) Notice: Subject to any disclaimer, the term of this patent is extended or adjusted under 35 U.S.C. 154(b) by 138 days.

(21) Appl. No.: 10/179,573

(22) Filed: Jun. 24, 2002

(65) Prior Publication Data

US 2003/0027215 A1 Feb. 6, 2003

Related U.S. Application Data

(60) Provisional application No. 60/300,589, filed on Jun. 22, 2001.

(51) Int. Cl.⁷ .............................. B01D 15/08
(52) U.S. Cl. ............... 210/656; 210/659; 210/143; 210/198.2; 73/61.52; 436/161
(58) Field of Search ............... 210/635, 656, 210/659, 143, 198.2; 73/61.52; 422/70; 436/161

(56) References Cited

U.S. PATENT DOCUMENTS

| | | | |
|---|---|---|---|
| 4,869,093 A | 9/1989 | Gilbert | 73/23.1 |
| 5,824,485 A * | 10/1998 | Thompson et al. | 435/6 |
| 5,922,541 A * | 7/1999 | Lee et al. | 435/6 |
| 5,938,932 A | 8/1999 | Connelly et al. | 210/659 |
| 6,004,617 A | 12/1999 | Schultz et al. | 427/8 |
| 6,087,475 A * | 7/2000 | Lee et al. | 530/324 |
| 6,175,409 B1 | 1/2001 | Nielsen et al. | 356/337 |
| 6,260,407 B1 | 7/2001 | Petro et al. | 73/61.52 |
| 6,265,226 B1 | 7/2001 | Petro et al. | 436/180 |
| 6,294,388 B1 | 9/2001 | Petro | 436/8 |
| 6,296,771 B1 | 10/2001 | Miroslav | 210/656 |
| 6,406,632 B1 | 6/2002 | Safir et al. | 210/656 |
| 6,439,036 B1 | 8/2002 | Mansky et al. | 73/61.41 |
| 6,455,007 B1 | 9/2002 | Mansky et al. | 422/101 |
| 6,632,404 B1 | 10/2003 | Freitag et al. | 422/100 |
| 6,635,668 B1 * | 10/2003 | Tidwell et al. | 514/394 |
| 2002/0124897 A1 | 9/2002 | Bergh et al. | 137/885 |

FOREIGN PATENT DOCUMENTS

| | | | |
|---|---|---|---|
| EP | 1089074 | 4/2001 | G01N/30/46 |
| EP | 0886143 | 3/2002 | G01N/33/68 |
| WO | WO 97/01755 | 1/1997 | G01N/30/46 |
| WO | WO 98/59360 | 12/1998 | H01J/49/04 |
| WO | WO 99/51980 | 10/1999 | G01N/30/02 |
| WO | WO 01/02452 | 1/2001 | C08F/292/00 |

OTHER PUBLICATIONS

Antworth et al., Org. Geochem. (1989), 14 (2), 157–164.
Brissova et al., Anal. Biochem. 242 (1996), 104–111.
Jerebak et al., Chromatographia 36 (1993), 259–262.
Kaneko et al., Energy Fuels (1996), 10 (4), 1017–1021.
Meyers, Marc Alan. Interactions between citrus flavor solutes and low density polyethylene by static and inverse–high pressure liquid chromatographic methods [dissertation]. New Brunswick (NJ): Rutgers State University; 1987. 207p. Available from: University Microfilms, Ann Arbor, MI; DA8723273.
Morino et al., Energy Fuels (1996), 10 (4), 1012–1016.
Morino et al., Sekitan Kagaku Kaigi Happyo Ronbunshu (1993), 30th, 122–125.
Morino et al., Sekitan Kagaku Kaigi Happyo Ronbunshu (1994), 31$^{st}$, 201–203 Abstract Only.
Petro et al., Reactive Polymers 23 (1994), 173–182.
Schram et al., J. Liquid Chromatography, 3 (3), (1983), 403–417.
Takanohashi et al., Conf. Proc. Int. Conf. Coal Sci, 7th (1993), 1, 419–422.

* cited by examiner

*Primary Examiner*—Ernest G. Therkorn

(57) ABSTRACT

Methods and apparatus for the evaluation of interactions between substances using inverse chromatography are disclosed. Preferably, interactions are evaluated between a liquid test sample and a solid phase comprising a receptor in the presence of a liquid carrier. Preferably, one of the modifying agent or receptor are members of a combinatorial library.

31 Claims, 4 Drawing Sheets

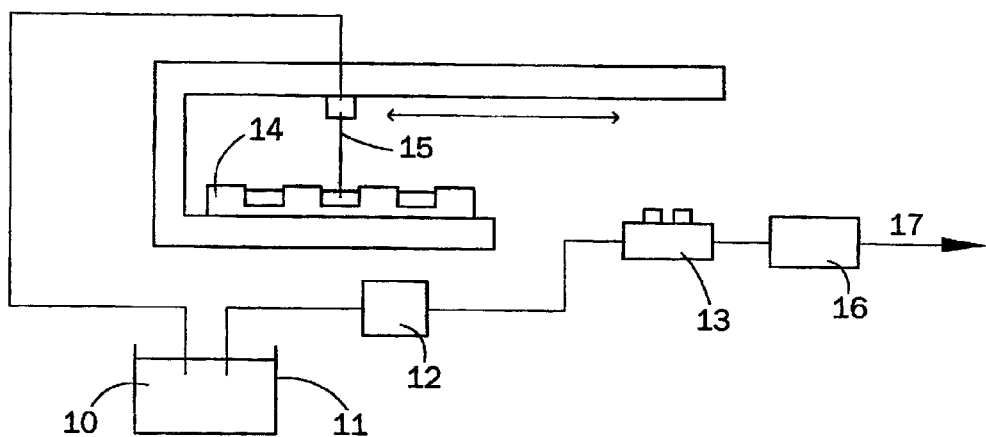
FIG. 1
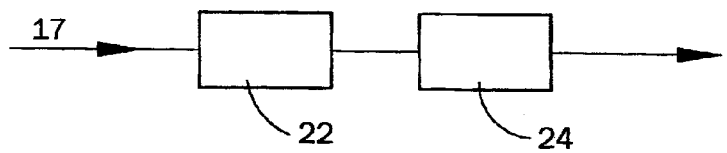
FIG. 2
FIG. 3
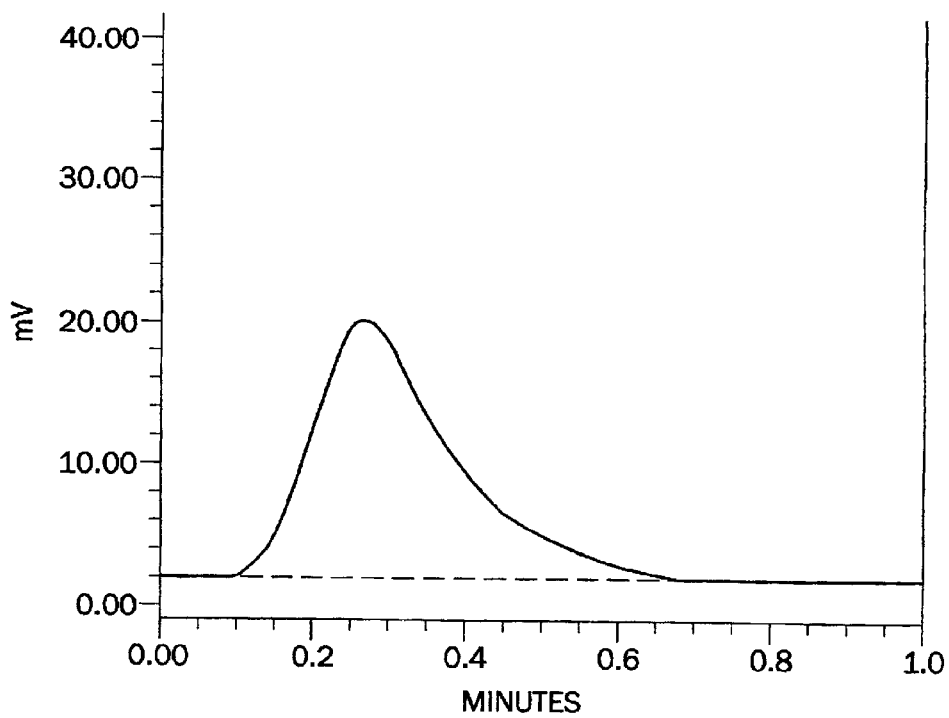

US 6,726,843 B2

INVERSE CHROMATOGRAPHY METHODS AND APPARATUS FOR EVALUATION OF INTERACTIONS BETWEEN MODIFYING AGENTS AND RECEPTORS COMPRISING NATURAL OR ARTIFICIAL MAMMALIAN TISSUE

This application is related to, and claims priority under 35 U.S.C. Sec. 119(e) to co-owned, co-pending U.S. provisional application Ser. No. 60/300,589 entitled "Evaluation of Interactions Between Substances" filed Jun. 22, 2001 by Petro et al.

BACKGROUND OF THE INVENTION

1. Field of the Invention

This invention relates to the evaluation of interactions between substances using inverse chromatography methods and apparatus. The term "substance" is used herein, i.e. throughout this specification, to mean a single element or compound, or a mixture of elements and/or compounds. The invention is particularly (but not exclusively) useful in the field of combinatorial science.

2. Introduction to the Invention

In the field of combinatorial science, there is a continuing need for improved methods for characterizing the members of libraries of substances.

The techniques of chromatography are well-known. In one widely used technique, often referred to as liquid solid chromatography, a liquid carrier (the "mobile phase") is passed over a solid (the "stationary phase") in a column. A sample is injected into the mobile phase before the mobile phase enters the column. The sample comprises at least one substance which interacts with the solid. The rate at which the substance migrates through the column depends on its relative affinity for the mobile and stationary phases. The technique can be used to separate two substances with different relative affinities for the phases, to characterize an unknown sample (using one or more known solids), or (in the process sometimes referred to as inverse chromatography) to characterize a known solid (using one or more known samples). Reference may made for example to U.S. Pat. No. 4,869,093 (Gilbert); J. Liquid Chromatography, 3 (3), (1983), 403–417, Schram et al.; Org. Geochem. (1989), 14 (2), 157–164, Antworth et al; Chromatographia 36 (1993), 259–262, Jerebak et al.; Sekitan Kagaku Kaigi Happyo Ronbunshu (1993), 30th, 122–125 (Morino et al.); Conf. Proc. Int. Conf. Coal Sci, 7th (1993), 1, 419–422, Takanohashi et al.; Energy Fuels (1996), 10 (4), 1012–1016, Morino et al.; Energy Fuels (1996), 10 (4), 1017–1021, Kaneko et al.; Anal. Biochem. 242 (1996), 104–111; Brissova et al; and Reactive Polymers 23 (1994), 173–182 Petro et al. Reference may also be made to U.S. Pat. Nos. 6,175,409, 6,406,632, 6,265,226, 6,260,407, 6,294,388 and PCT Publication WO 99/51980. The entire disclosure of each of the patents, publications and patent applications referred to above is incorporated herein by reference for all purposes.

SUMMARY OF INVENTION

This invention relates to methods and apparatus which are useful for evaluating the interaction between a receptor and a modifying agent in the presence of a liquid carrier, and which make use of novel and inventive variations of the known techniques of liquid solid chromatography. In the terminology often used in chromatography, the invention includes (but is not limited to) methods in which the receptor is the probe and the modifying agent is the sample, and methods in which the modifying agent is the probe and the receptor is the sample.

In a first aspect of the invention, one of the receptor, modifying agent and liquid carrier is a member of a library, preferably either the receptor or modifying agent is a member of a library, and in either case, the method includes evaluating members of the library in a number of test procedures, and using the results of test procedures to select at least one substance for further testing. The substance selected for further testing will generally be a member of the library, but may be a substance having a known relationship to a member of the library.

In other aspects, the invention provides various methods which are useful as test procedures in the first aspect of the invention, but which are also useful in other contexts, for example for evaluation of interaction between substances by inverse chromatography, and for the rapid testing of a sample withdrawn from a continuous process. In yet further aspects, the invention provides apparatus suitable for carrying out the methods of the invention.

The term "evaluating" is used herein in a broad sense to denote any useful assessment of the interaction between the receptor and the modifying agent. For example, in the first aspect of the invention, the term includes any assessment which makes it possible to select at least one substance for further testing. The term "receptor" is used herein to denote a substance which can form at least part of a solid phase. Thus, the receptor, alone or in combination with a solid, corresponds generally to the stationary phase in conventional liquid solid chromatography. The term "liquid carrier" is used herein to denote any liquid which can be passed continuously over the solid comprising the receptor while the solid is confined in a test chamber. Thus, the liquid carrier corresponds generally to the mobile phase in conventional liquid solid chromatography. The term "modifying agent" is used herein to denote a substance which can form at least part of a liquid sample which can be injected into a stream of the liquid carrier before the stream is passed over the solid in the test chamber. The term "library" is used herein in a broad sense to denote a plurality of identified substances, typically an associated collection of identified substances. The library is preferably a spatially determinate array of identified substances formed at or in or situated on a common substrate. Preferably, but not necessarily, the members of the library differ from each other in some systematic way, so that the variation of the results of the test procedures can be correlated with those differences. For example, the members can differ from each other in one or more quantified ways. Such differences can be quantified by measurements carried out during preparation of the substances, or by measurements carried out on the substances themselves. The differences can be ascertained before or after members of the library have been selected in accordance with the present invention.

The method of the first aspect of the invention comprises conducting a plurality of test procedures, each of the test procedures comprising the steps of (a) injecting a liquid test sample comprising the modifying agent into a stream of the liquid carrier, the injection being carried out over a limited time so that a distinct test section of the stream contains the test sample;

(b) passing the stream of liquid carrier containing the test sample over a solid phase in a test chamber, the solid phase comprising the receptor; and (c) examining the stream of liquid carrier leaving the test chamber to ascertain a variable which reflects the interaction of the modifying agent and the receptor in the presence of the liquid carrier.

Step (c) of the method will often comprise examining a distinct evaluation section of the stream corresponding to the test section in order to ascertain a property of the modifying agent. The term "to ascertain a property of the modifying agent" is used herein to include ascertaining a property of the modifying agent itself and/or ascertaining a property of a substance which is produced by the interaction of the modifying agent and the receptor and/or ascertaining a property of part only of the modifying agent.

The results obtained in the steps (c) of the test procedures can optionally be used to select at least one substance for further testing. The further testing can for example involve the interaction between (i) a selected member or members of the library and (ii) the other two of the receptor, modifying agent and liquid carrier used in the test procedures. The further testing can otherwise be unrelated to the original evaluation.

The term "examining the stream of liquid carrier leaving the test chamber to ascertain a variable which reflects the interaction of the modifying agent and the receptor in the presence of the liquid carrier" is used herein in a broad sense to denote any examination which enables the desired evaluation to be made. For example, as further explained below, it may be sufficient to compare the results of the test procedures without quantifying any property of the modifying agent. Preferably (but not necessarily) step (c), alone or in combination with other steps, makes it possible to calculate the proportion of the modifying agent, or a component of the modifying agent, retained in the test chamber.

The objective of the known chromatographic procedures is (i) to achieve at least some separation of the individual components of the sample, followed by collection of at least one separated product, and/or (ii) to achieve a substantial degree of equilibration between the sample and the stationary phase in order to provide detailed characterizing data. The known procedures use, therefore, combinations of stationary and mobile phases, processing times, and columns which achieve these objectives. By contrast, it is not an objective of the present invention to recover a separated product or to achieve equilibrium between the sample and the solid phase. Furthermore, in the first aspect of the invention, the library is preferably examined as quickly as is consistent with selection of a limited number of members for further testing and under dynamic conditions which simulate an ultimate end-use. For example, the objective might be to identify the members of a library having the potential to be additives which produce a desired effect on a fabric being laundered or dry cleaned, or on photographic film being developed, or in a paint being applied to a building material.

Because of these differences in objectives, the test procedures used in the first aspect of the invention often have at least one (i.e. one or more) of the following characteristics which distinguish them from known chromatographic procedures.

(I) The receptor is a substance which has not been used as the stationary phase in liquid solid chromatography. For example, the receptor comprises
  (1) a fabric,
  (2) at least 50% by weight of particles having an aspect ratio of at least 2 and at least one dimension which is greater than 100 micron,
  (3) a substantially pore-free sheet of an organic polymer,
  (4) a foodstuff,
  (5) a natural or artificial mammalian tissue,
  (6) a polysaccharide, a protein or a nucleic acid,
  (7) a catalyst,
  (8) an elemental metal or metal alloy,
  (9) wood,
  (10) concrete,
  (11) natural or artificial stone,
  (12) a semiconductor substance, or
  (13) a DNA chip, a molecular recognition chip, or a separation chip.

The receptor material preferably includes mammalian tissue, either artificial or natural. Other preferred receptor materials are selected from the group consisting of a fabric, a substantially pore-free sheet of an organic polymer, a foodstuff, wood, concrete, natural or artificial stone, and a semiconductor substance. Within this group, receptor materials selected from a fabric, a foodstuff and a semiconductor substance are particularly preferred.

(II) The test chamber is less efficient than columns used in liquid solid chromatography. For example, the efficiency of the test chamber is less than 80, preferably less than 50, particularly less than 10, theoretical plates.

(III) The test procedures are carried out rapidly and under dynamic conditions. These dynamic conditions are not intended to promote separation of the modifying agent into component parts or to ensure that all of the modifying agent passes through the test chamber. Furthermore, the extent of the interaction between the receptor and the modifying agent can vary widely in the different test procedures. As a result, one or more of the following conditions are often fulfilled.
  (1) In each of the test procedures, the test sample comprises an initial quantity of the modifying agent, and in at least one of the test procedures at least 1%, often at least 10%, e.g. 20–70% or 30–50%, of the initial quantity of the modifying agent is retained in the test chamber. Substantially all of the modifying agent retained until the end of a test procedure remains retained on the solid phase during subsequent test procedures, and thus can be regarded as being irreversibly retained on the solid phase under the test conditions.
  (2) In each of the test procedures, the test sample comprises an initial quantity of the modifying agent, and the difference between (i) the lowest percentage of the initial quantity of modifying agent retained in the test chamber in any of the test procedures and (ii) the highest percentage of the initial quantity of modifying agent retained in the test chamber in any of the test procedures, is at least 10, for example 10–70, often at least 25, for example 30–60.
  (3) In at least one, preferably in each, of the test procedures, the receptor is not saturated by the modifying agent. The extent to which saturation is being approached can be assessed by repeating one of the test procedures. Preferably, in such a repeated test procedure, the same proportion of the modifying agent is retained by the receptor, indicating that the receptor is far from saturation. If a lesser proportion is retained, this indicates that the receptor is approaching saturation; and when none of the modifying agent is retained, the receptor is saturated.
  (4) In at least one, preferably in each, of the test procedures, a plot of time against concentration of the modifying agent in the stream of liquid carrier leaving the test chamber has only a single peak, with the slope of the plot being positive at all points on one side of the peak and negative at all points on the other side of the peak.

(5) In at least one, preferably in each, of the test procedures, the stream of liquid leaving the test chamber is passed through a detector, and the time taken for the evaluation section to pass through the detector is less than five times the time taken for the test section containing the modifying agent to pass through the entrance to the test chamber.

(IV) The desired evaluation is carried out merely by ascertaining the proportion of the modifying agent which is retained in the test chamber (i.e. it is unnecessary to know, in absolute terms, the quantity of modifying agent initially present in the sample). This makes it possible to carry out the desired evaluation by comparing (a) the results of passing the sample-carrying liquid stream through the test chamber and (b) the results of a reference procedure in which a similar sample-carrying liquid stream is passed through a reference chamber which (i) is free of any substance which interacts with the modifying agent, or (ii) contains a known solid substance. In some cases, satisfactory results can be obtained by comparing the results of each of the test procedures with a single reference procedure or with two or more reference procedures which are carried out at appropriate intervals. However, this requires a uniformity between the different procedures which is not always easy to attain. It is preferred, therefore, that each of the test procedures should itself incorporate the reference procedure. In this case, each of the test procedures further comprises (d) injecting a liquid reference sample into a second stream of the liquid carrier, the composition of the second sample being substantially identical to the composition of the test sample, and the injection being carried out over a limited time so that only a distinct reference section of the stream contains the reference sample;

(e) passing the second stream of liquid carrier containing the reference sample through a reference chamber which is free of any substance which interacts with the modifying agent;

(f) examining the stream of liquid carrier leaving the reference chamber to ascertain a property of the modifying agent remaining in the stream; and (g) comparing the results obtained in steps (c) and (f) to evaluate the interaction between the receptor and the modifying agent.

In the aforementioned protocol, the second stream into which the reference sample is injected can be the same stream into which the test sample was injected (or alternatively, can be a separate and independent stream (i.e., a separate line)). Preferably, therefore, the first liquid stream containing the test section and second liquid stream containing the reference section are obtained by (i) injecting into the stream of liquid carrier a liquid unit whose composition is the same as the composition of the test and evaluation samples and whose size is equal to the sum of the sizes of the test and evaluation samples, the injection being carried out over a limited time so that only a distinct section of the liquid stream contains the liquid unit, and (ii) splitting the liquid stream containing the liquid unit into a first sub-stream which passes through the test chamber and includes the test section and a second sub-stream which passes through the reference chamber and includes the reference section.

In the methods of the first aspect of the invention, the test procedures can be carried out in series or in parallel or both.

In some embodiments, it is particularly preferably to use parallel (simultaneous) procedures, especially with respect to applications in combinatorial materials science, in which either the library or receptors are members of a combinatorial library comprising at least four members, such that members are evaluated for interaction between a receptor member of the combinatorial library and a modifying agent, or alternatively for interaction between a modifying agent member of a combinatorial library and a receptor, in each case in the presence of a liquid carrier. Preferably each of the at least four members of the combinatorial library comprise a different non-biological polymer. The method includes conducting at least four test procedures in parallel under a common set of test conditions, with the receptor, modifying agent and liquid carrier being the same in each of the test procedures except that in each test procedure a different member of the combinatorial library is used.

The parallel testing/evaluation can include multiple flow channels with simultaneous contacting of test samples (comprising a modifying agent) and solid phases (comprising a receptor) as compared between different channels. The injection into such parallel-configured carrier streams, each having its own dedicated test chamber, can be accomplished in a sequential manner, as described for example in co-owned U.S. Pat. No. 6,296,771. Alternatively, the injection into such parallel-configured carrier streams can also be accomplished in parallel, using parallel injection systems such as are disclosed in co-owned, co-pending U.S. applications, Ser. No. 09/641,442 filed Aug. 2, 2002 by Freitag et al. and Ser. No. 10/092,035 filed Mar. 6, 2002 by Bergh et al. In either case, the detection (examining step) is preferably done in parallel, but can also be sequential. In a preferred protocol, the at least four parallel test procedures can comprise:

(a) simultaneously injecting at least four liquid test samples comprising an initial quantity of the modifying agent into at least four separate and distinct streams of the liquid carrier, respectively, the injections being carried out over a limited time so that distinct test sections of the at least four streams contain the test sample, (b) simultaneously passing the at least four streams of liquid carrier containing the test samples over a solid phase in at least four separate and distinct test chambers, respectively, the solid phase comprising the receptor, (c) retaining at least 10% of the initial quantity of the modifying agents on the solid phase in each of the at least four test chambers, the retained modifying agents being irreversibly retained under the test conditions of the procedures, and (d) simultaneously examining the at least four streams of liquid carrier leaving the test chamber to ascertain, for each of the at least four streams, a variable which reflects the interaction of the modifying agent and the receptor in the presence of the liquid carrier for that respective stream, and (e) comparing the interaction of the modifying agent and the receptor for each of the at least four streams to determine a relative ranking of the members of the combinatorial library with respect to such interaction.

It is specifically contemplated that such parallel methods, and in particular the above-detailed preferred parallel methods for evaluation of combinatorial libraries can be used in connection with each and every other embodiment disclosed herein (e.g., evaluating interaction between a modifying agent and a receptor comprising natural or artificial mammalian tissue, or other types of materials (as listed above), evaluation protocols involving a reference chamber, etc.)— such as test procedures (I) to (IV) as outlined above.

Individual test procedures having one or more of characteristics (I) to (IV) set out above are in themselves novel and inventive, and form part of the present invention. Thus, in second to fifth aspects, the present invention provides methods which are suitable for evaluating the interaction between a receptor and a modifying agent in the presence of a liquid carrier and which respectively have one of characteristics (I) to (IV) set out above.

In a sixth aspect, the invention provides apparatus suitable for carrying out the method of the first aspect of the invention wherein the modifying agent is one of the library and each of the test procedures has characteristic (I) above, the apparatus comprising (A) a test chamber for the solid phase comprising a receptor as defined in characteristic (I) above;

(B) a reservoir for the liquid carrier;

(C) a pump for continuously extracting a stream of the liquid carrier from the reservoir and passing the stream through the test chamber;

(D) an autodilution and sampling robot for sequentially injecting into the stream of liquid carrier, before the stream passes through the chamber, a plurality of liquid test samples, each sample containing an initial quantity of one of the library of modifying agents and each sample being injected over a limited time so that only a distinct test section of the liquid stream contains the sample; and (E) a detector for examining the stream of liquid carrier leaving the test chamber without removing anything from the stream and for determining for each sample the proportion of the initial quantity of the modifying agent remaining therein.

In a seventh aspect, the invention provides apparatus suitable for carrying out the method of the first aspect of the invention wherein the method has characteristic (II) above, the apparatus comprising a test chamber which contains the solid phase comprising the receptor and which has an efficiency of less than 80, preferably less than 50, especially less than 10, theoretical plates; and a reservoir, pump, autodilution and sampling robot and detector as in the apparatus of the seventh aspect of the invention.

In an eighth aspect, the invention provides apparatus which is suitable for carrying out the method of the first aspect of the invention wherein the method has characteristic (IV) as defined above, and which comprises (A) a test chamber containing the solid phase comprising the receptor;

(B) a reference chamber which is free of any substance which interacts with the modifying agent;

(C) a reservoir for the liquid carrier;

(D) a main passageway from the reservoir;

(E) a first branch passageway which is connected to the main passageway has a junction and which leads from the main passageway to the test chamber;

(F) a second branch passageway which leaves from the test chamber;

(G) a third branch passageway which is connected to the main passageway at the junction and which leads from the main passageway to the reference chamber;

(H) a fourth branch passageway which leaves from the reference chamber;

(I) an exit passageway which combines the second and fourth branch passageways;

(J) a pump for extracting a stream of the liquid carrier from the reservoir and passing it through the main passageway;

(K) an injector for injecting into the stream of liquid carrier, before the stream passes from the main passageway to the first and third branch passageways, a liquid unit containing an initial quantity of the modifying agent, the unit being injected over a limited time so that only a distinct section of the liquid stream contains the unit, and the sample being divided into a first sub-stream which contains a first sample of liquid unit and which passes through the test chamber and a second sub-stream which contains a second sample of the liquid unit and which passes through the reference chamber; and (L) a detector for examining the stream of liquid carrier passing out of the exit passageway and for ascertaining the proportion of the modifying agent remaining therein.

BRIEF DESCRIPTION OF THE DRAWINGS

The invention is illustrated in the accompanying drawings, which are described briefly as follows.

FIG. 1 is a diagrammatic illustration of an apparatus for injecting a plurality of liquid units into a stream of liquid carrier;

FIGS. 2, 4, 6, 9, 10 and 11 are diagrammatic illustrations of apparatus for evaluating the interaction between a receptor and a library of modifying agents, by passing a stream containing successive samples of the library through a chamber containing the receptor, and examining the stream leaving the chamber with a detector, the apparatus of FIG. 11 also being suitable for evaluating the interaction between a modifying agent and a library of receptors; and FIGS. 3, 5, 7 and 8 are plots of time against the amount of modifying agent remaining in the stream leaving the chamber, as recorded by the detectors in FIGS. 2, 4, 6, 9, 10 and 11.

DETAILED DESCRIPTION OF THE INVENTION

Figure 4:
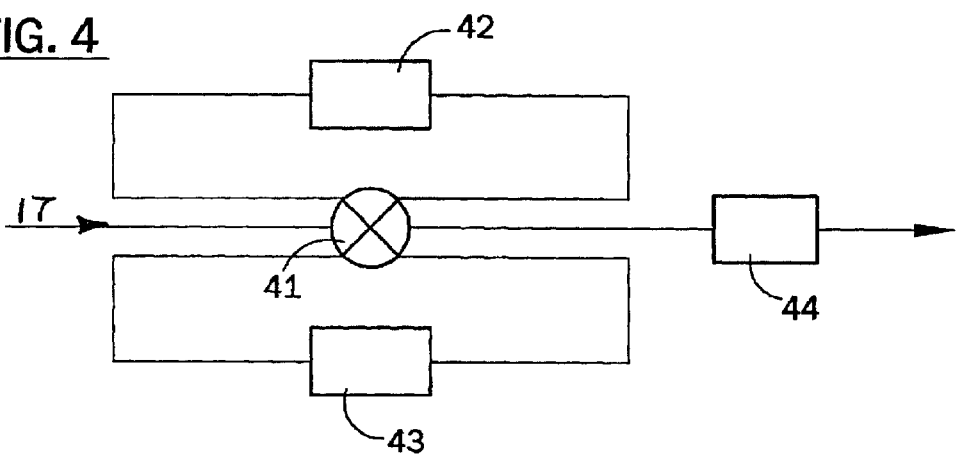

In the Summary of the Invention above, the Detailed Description of the Invention, the Examples, and the Statements below, and the accompanying drawings, reference is made to particular features of the invention. It is to be understood that the disclosure of the invention in this specification includes all appropriate combinations of such particular features. For example, where a particular feature is disclosed in the context of a particular embodiment, a particular statement, or a particular Figure, that feature can also be used, to the extent appropriate, in the context of other particular embodiments, Statements and Figures, and in the invention generally.

The detailed description below is directed to each aspect of the invention, considered individually and in various combinations. Aspects of the detailed description are chiefly directed to the first aspect of the invention, in which libraries of compositions are evaluated, and to apparatus for use in the first aspect of the invention. It is to be understood, however, that insofar as the detailed description is concerned with test procedures having one or more of the characteristics (I) to (IV) above, it is also applicable to the second to sixth aspects of the invention.

Receptors

The receptor can be any element, compound or composition which is a solid or which can be immobilized on a solid. Receptors that are suitable, and indeed in some embodiments preferred, include the following.

(1) Fabrics (i.e., a fabric material), including woven, knitted and non-woven fabrics (including papers), made from natural or artificial (including regenerated natural) sources, such as continuous filament or staple fiber yarns, for example polyamide, polyester, polyolefin, polyurethane, cellulosic, cotton, silk and wool yarns. The particular form of the fabric material is not narrowly critical, and can include sheets of fabric materials, bulk fabric materials, stranded fabric materials (e.g. yarns), etc.

(2) Particulate materials, including particulate materials which comprise at least 50%, preferably at least 75%, e.g. 75–100%, by weight of particles having an aspect ratio of at least 2, preferably at least 5, particularly at least 10, especially at least 50, e.g. at least 100, and optionally having at least one dimension greater than 100 micron, preferably greater than 500 micron.

(3) Continuous sheets of natural or synthetic (including regenerated natural) organic polymers, including such sheets which are free of open pores and preferably are substantially free of all pores.

(4) Foodstuffs, including coffee beans (green and roasted), ground coffee, meats, poultry, beans (e.g., soybeans), grains, cereals, rice, pastas, fruits and vegetables.

(5) Natural and artificial mammalian tissues, including for example human or animal epidermis, epithelium, bone and hair. More generally, the receptors of the invention can comprise biological tissue, including both natural and artificial biological tissue. A more specific description of the mammalian tissue and/or more generally, the biological tissue of the invention is set forth as follows.

(5a) The biological tissue (especially mammalian tissue) can include both natural and non-natural model biological tissue, as well as both hard biological tissue and soft biological tissue. Details discussed hereinafter with regard to biological tissue, is particularly intended to refer to mammalian tissues. In general, biological tissue can be naturally occurring animal biological tissue or non-natural biological tissue (including both non-natural materials and natural materials that are not natural biological tissues). Also, in general, it is preferred that the biological tissues used in the arrays and methods of the present invention are soft biological tissues and/or hard biological tissues. These tissues should preferably, in each case, fulfill the following requirements: (i) they should be chemically and physically similar to human tissues (e.g., with respect to properties of interest, such as polymer adsorptivity), and (ii) and they should be suitable for high-throughput screening (e.g., with respect to availability in sufficient quantities and reproducability to allow for comparison between experiments of the screen).

(5b) A natural biological tissue can be an animal biological tissue, and in many cases, is preferably a human biological tissue, but can also be an animal biological tissue such as bovine, porcine (pig), etc. Exemplary natural oral tissues include tissues from the tongue, teeth, heart, lungs, liver, kidney, spleen, brain vein, skin, blood, muscle, hair, etc. of animals, especially mammals such as humans and non-human mammals, and especially of non-human mammals such as non-human primates, porcine (pig), bovine, rabbit, and mice, among others. For oral care applications, for example, exemplary natural oral tissues include human teeth (as an exemplary natural hard oral tissue), or tongue, such as porcine (pig) tongue (as an exemplary natural soft oral tissue), or gum, such as bovine or porcine gum (as an exemplary natural soft oral tissue) or cheek lining, such as bovine cheek lining (as another exemplary soft oral tissue).

(5c) A model biological tissue can include both non-natural materials, and natural materials that are not natural biological tissues. Model biological tissues preferably can have substantially the same chemical properties as natural human biological tissue, particularly in an environment that is representative of the in-vivo conditions for the biological tissue of interest. In particular, the model biological tissue is preferably effective for emulating natural animal biological tissue (e.g., natural human biological tissue or natural bovine biological tissue or natural porcine biological tissue) for polymer adsorption to the biological tissue, typically in the presence of a composition or atmosphere that is representative of, or emulates the natural composition or atmosphere in which the biological tissue is found. Especially, the model biological tissue is preferably effective for emulating natural oral tissue for polymers already known in the art as having a certain degree of interaction, such as adsorptivity, with that biological tissue. For example, in oral care applications, the model oral tissue is preferably effective for emulating natural oral tissue for polyoxyalkylene polymer adsorption to the tissue in the presence of natural or artificial saliva. Preferably, as determined using the evaluation protocol of choice (e.g., as described above), the degree of adsorptivity between the model biological tissue and the polymer of choice in the presence of the conditions that emulate the in vivo conditions for the tissue, can be comparable within at least about 50%, preferably at least about 30%, more preferably at least about 10%, and most preferably at least about 5%, as compared to the degree of adsorptivity between polymer and the natural animal biological tissue in the presence of such conditions. Exemplary model biological tissues include porous man-made polymeric materials (as an example of non-natural model biological tissues), mineral-based materials (as an example of natural or non-natural model hard tissues), epidermal (skin) or epithelium cells or other cells or soft tissue (as an example of a natural material that is not a natural oral tissue for a model soft oral tissue). More specific examples, for oral care applications, of model oral tissues include hydroxyapatite (as an example of a model hard oral tissue) and reconstructed epithelium (as an example of a model soft oral tissue).

(5d) For oral care applications, the oral tissue used according to the present invention is preferably selected from the group, consisting of a soft oral tissue, such as an animal tongue, especially a pig tongue (emulating human tongue), a reconstructed epithelium (emulating human soft tissue such as cheek lining or gum), and a hard oral tissue, such as animal teeth, especially human teeth, and hydroxyapatite (emulating human teeth). Pig tongue provides reproducible results in high-throughput screening experiments and is a reliable substrate for high-throughput screening purposes. The surface area of pig tongue is high enough to provide sufficient sensitivity to distinguish between adsorptivity of various polymers. Epithelium reconstructed from human cells is commercially available from SkinEthics (France). Reconstructed epithelium also provides reproducible results in high-throughput screening experiments. The reconstructed epithelium may be used in the form of small pieces provided on the bottom of the wells of a microtiter plate, or in the form of strips of a larger piece of epithelium. Human teeth are available from dental offices or other dental supply sources, or from kids having ages ranging from about 4 to about 10 years, preferably from about 5 to about 7 years. If the array of the present invention comprises hydroxyapatite (HAP), the form of the HAP is not narrowly critical, and can be varied depending on the application of interest. For example, the HAP can be in the form of a sheet, disc, or powder. HAP powder or HAP in the form of discs is commercially available (Clarkson Chromatography Products, Inc.; South Williamsport, Pa.). HAP powder is preferred for some applications, and can comprise particles having a size ranging from about 1 pm to about 100 pm, preferably from about 5 pm to about 50 pm, and in general, can more preferably consist essentially of particles having a size ranging in these same ranges. A preferred HAP powder comprises or consists essentially of porous HAP particles having a particle size of from 10 to 30 pm, preferably about 20 pm. HAP powder has a high surface area of about 7 to 8 $m^2/g$ (measured in accordance with the BET method and mercury porosimetry) and is characterized by the ability to average differences among the individual HAP particles in a certain volume of the powder. Moreover, HAP powder does not show a significant fluorescent background. Therefore, quantitatively strong signals may be obtained. HAP powder is preferably used in the present invention. HAP discs have a thin porous layer at the surface only and, therefore, are practically impermeable. The surface area of HAP discs is about 0.1 $m^2/g$.

(6) Compositions comprising a polysaccharide, protein (i.e. an amino acid polymer, including peptides, enzymes, biologically functional proteins, etc.) or nucleic acid (i.e., a nucleic acid polymer, including deoxyribonucleic acid, ribonucleic acid, oligonucleotides and biologically functional nucleic acid polymers). In particular, such compositions are preferred in combination with one or non-biological polymers (e.g. provided as supports, linkers, brushes or otherwise. For example, the receptor can comprise a polysaccharide, protein (i.e., amino acid polymer) or nucleic acid (i.e., nucleic acid polymer) as a biological probe, where the probes are presented using specifically designed non-biological polymer brushes (e.g., polymer-coated surfaces prepared for example through living free radical polymerization techniques). Such biological compositions presented on polymer brushes are described in co-owned PCT application WO 01/02452, and in the corresponding co-owned U.S. applications, Ser. Nos. 09/347,606, 09/347,607, 09/347,608 and 09/347,609, each of which is incorporated herein by reference for all purposes.

(7) Catalyst, including catalyst comprising a metal, e.g. a transition metal or a Group IV metal, or a metal compound, or a protein, optionally supported by an in the support, e.g. a support composed of a silicate, a zeolite, alumina or another metal oxide.

(8) Elemental metals and metal alloys.

(9) Building materials including wood, concrete, natural stone and artificial stone.

(10) Semiconductors.

(11) DNA chips, molecular recognition chips, and separation chips. DNA chips, as used herein, refer to an array of different deoxyribonucleic acid polymer molecules formed on, residing on, or supported by or in a common substrate. Molecular recognition chips refer to an array of different compounds or compositions that are selective for (i.e., selectively recognize) a particular chemical entity of interest, with such compounds or compositions being formed on, residing on or supported by or in a common substrate. An example of a molecular recognition chip can include an arrays of monoclonal antibodies formed on a common substrate. Separation chips refer to array of different compounds or compositions that are functional for separating (e.g., by size, by charge, by chemical composition, etc.) components of a mixture (e.g. components of a test sample), with such compounds or compositions being formed on, residing on or supported by or in a common substrate.

Modifying Agents

The modifying agent can be any composition which can form at least part of a liquid sample and which will interact with the receptor. The sample generally comprises a liquid in which a solid or fluid modifying agent is dissolved, dispersed or emulsified. The liquid in the sample preferably does not interact with the receptor, and is preferably the same as the liquid carrier. The concentration of the modifying agent in the sample is generally 0.001 to 10% by weight, preferably 0.05 to 0.5% by weight.

Often the interaction between the receptor and the modifying agent will be merely physical adsorption of the modifying agent on the surface of the receptor. However, the interaction can alternatively or additionally involve other types of interaction, including for example Lewis acid/Lewis Base interaction, hydrogen bonding, occlusion, and clathration. In the first aspect of the invention, the objective is generally to identify the combinations of receptor, modifying agent and liquid carrier which result in the greatest retention of the modifying agent in the test chamber. It is preferred, therefore, that in the least one of the test procedures, at least 10%, particular least 20%, e.g. 20–70%, or 30–50%, of the initial quantity of the modifying agent is retained in the test chamber. The variation in the results of the test procedures may be for example such that there is a difference of least 10, for example 10–70, often at least 25, for example 30–60, between (i) the percentage of the initial quantity of the modifying agent retained in the test chamber in one of the test procedures and (ii) the percentage of the initial quantity of the modifying agent retained in the test chamber in another of the test procedures.

Organic polymers, including non-biological polymers and synthetic polymers, are preferred modifying agents. The polymer can be, for example, crystalline or non-crystalline, a thermoplastic or an elastomer, (including a thermoplastic elastomer), and a homopolymer or copolymer, for example a polyamide, a polyester, a polyurethane, a polyether, a polyurea, or a polymer comprising units derived from at least one ethylenically unsaturated monomer, e.g. an olefin, a vinyl monomer, or acrylic or methacrylic acid or an ester or amide thereof. Suitable polymers include polymers containing polar groups, e.g. a hydroxyl group, a primary, secondary or tertiary amino group (substituted or unsubstituted), or a carboxyl, sulfonyl or other acidic group or a salt or ester thereof.

The modifying agents of the invention can also include therapeutic agents and/or diagnostic agents, themselves, and/or in combination with non-biological polymers (i.e., non-biological organic polymers). As used herein, therapeutic agents includes prophylactic agents. Hence, the modifying agents can be chemical or biological entities that provide a diagnostic benefit for identifying or determining a particular state or condition such as a particular malady, medical concern or health concern, that provide a therapeutic benefit for a particular malady or medical concern or health concern, and/or that provide a prophylactic benefit, to avoid a particular malady or medical concern or health concern. When such therapeutic agents or diagnostic agents are used in combination with non-biological polymers, either the agents or the non-biological polymers or both can be members of a combinatorial library. In some embodiments, different non-biological polymers are preferably members of a combinatorial library being evaluated for interaction with a receptor, for example, such as a mammalian tissue, or other biological tissue.

When the modifying agent contains two or more compounds, including polymer molecules of different molecular weights, there may be some separation of those compounds as they pass through the test chamber. Such separation is not generally desired or useful for the purposes of the present invention and preferably does not take place. If such separation does take place, and the detector measures both the separated compounds, a plot of time against the concentration of the modifying agent in the stream leaving the test chamber will evidence that separation. In some cases, the plot will show more than one peak, each peak corresponding to one of the separated components of the modifying agent. Preferably the plot has a principal peak which, when the plot is subjected to valley-to-valley integration, amounts to at least 70%, preferably at least 80%, of the area under the curve. It is particularly preferred that the plot has only a single peak, with the slope of the plot being positive at all points on one side of the peak and negative at all points on the other side of the peak.

Liquid Samples

The liquid samples are preferably small in size, so that they can be injected in a very short time, e.g. a fraction of the second, into the stream of liquid carrier. For example, the volume of the liquid sample may be, for example from 1 to 500 microliters, preferably from 5 to 50 microliters. The samples are generally injected at a time interval of not more than 10 minutes, preferably one every 0.15 to 3 minute.

Liquid Carriers

The liquid carrier can be any liquid which can be passed over the solid phase in the test chamber and which permits satisfactory ascertainment of a property of the modifying agent. Generally, the liquid carrier can include water, aqueous solvents, non-aqueous polar solvents and/or non-polar solvents. Preferably, there will be substantially no interaction between the liquid carrier and the solid phase. The liquid carrier can be aqueous, organic or a mixture of miscible aqueous and organic liquids. Preferred liquid carriers are aqueous solutions of inorganic salts optionally containing surface active agents, e.g. laundry additives, particularly solutions of the kind found in clothes washing machines and dishwashers. Other liquid carriers are organic solvents of the kind used in the dry cleaning of clothes, optionally containing surface active agents. When the library is a library of liquid carriers, the liquid carriers can for example be aqueous solutions which differ from each other in pH or temperature or both.

Libraries

In each of the test procedures in the methods of the first aspect of the invention, one of the receptor, modifying agent and liquid carrier is a member of a library. In preferred embodiments, the library members are either receptors or modifying agents, such that members are evaluated for interaction between a receptor member of the combinatorial library and a modifying agent, or alternatively for interaction between a modifying agent member of a combinatorial library and a receptor, in each case in the presence of a liquid carrier. Regardless of the characterization of the library members, the library generally contains at least four members and may contain many more, for example up to 96 members. Sometimes all the members of the library are tested, but this is not necessary. Generally at least four test procedures are carried out, using a different member of the library in each test procedure. If not all the members of a library are tested, the tested members will generally be taken from different sections of the library. If not all members of a library are tested, the results of the steps (c) can be used to select one or more members of the library for further testing. The selected member(s) may be member(s) which were tested and/or member(s) which were not tested. Different library members may be screened simultaneously using the same test procedures (ie., screened under a common set of conditions using common protocols), and/or the different library members may be screened sequentially.

The invention is particularly useful when the library is a library of modifying agents, because it is then possible to use a conventional autodilution and sampling robot to inject the different test samples into the stream of liquid carrier (e.g., in sequential fashion). Furthermore, when, as is preferred, the surface area of the solid phase is relatively large by comparison with the amount of the modifying agent, the members of the library can be tested in series, with the stream of liquid carrier, containing the different samples in sequence, being passed through the same test chamber. This is particularly advantageous where each sample does not saturate the solid phase receptor. In this way, a rapid rate of testing can be maintained, and moreover, can be multiplied particularly if at least two, e.g. four or more, substantially identical test chambers are used in parallel. By contrast, when the library is a library of receptors, a plurality of test chambers, each containing a different receptor, can be individually prepared, and they are preferably tested in parallel. Alternatively, the plurality of different individual receptors can be presented for testing in a single flow-channel system by alternately and successively replacing one test chamber (comprising a solid phase having a receptor comprising one member of the library) with the next test chamber (comprising a solid phase having another receptor comprising another member of the library). When the library is a library of liquid carriers, they too can be tested in parallel, or with proper hardware configuration, in series.

When the library is a library of modifying agents, any appropriate diversity element can form the basis of the library. For example, the library of modifying agents can comprise four or more different therapeutic agents or can comprise four or more different diagnostic agents, especially for screening with biological tissue such as mammalian tissue. Other diversity elements are well known in the art, especially for small organic molecules, enantiomeric molecules and for molecules having biological and/or pharmaceutical activity. The library of modifying agents can, in any case, further comprise non-biological polymers. The same common non-biological polymers can be used in connection with the library (e.g., when a different chemical entity such as a therapeutic or diagnostic agent is employed as the diversity element of the library). Alternatively, and in one particularly preferred embodiment, the non-biological polymers can be the diversity element of the library, and can preferably (but not necessarily) be applied to a same common agent such as a same common diagnostic agent or therapeutic agent. The library of modifying agents can also have more than one diversity elements, including for example at least four members that vary with respect to two or more features (e.g. different non-biological polymer and different therapeutic and/or diagnostic agent).

The combinatorial library can be also be a library of receptors. The library of receptors can include different receptor materials. Hence, when the receptors comprise mammalian tissue, the library can comprise different natural or artificial mammalian tissue. The variation in the receptors as compared between members of such a library can include the specific nature of the tissue, the source of the tissue, the pretreatment history of the tissue, etc. The different receptor materials can, in a preferred embodiment, include different non-biological polymers to create diversity between members of the library. For example, a same common receptor material (e.g., mammalian tissue, fabric materials, etc.) can be pretreated (e.g. by coating, immersion, etc.) with a different non-biological organic polymer. In this way, various treatment agents and protocols for a given receptor (e.g. mammalian tissue, fabric materials) can be investigated to determine a preferred non-biological treatment agent and protocol. A specific example of such application relates to skin care and/or wound care, in which the receptor can comprise skin cells (e.g. epidermal cells, epithelium cells) that have been pretreated with various different non-biological polymers to form a library of different receptor materials. The different receptor materials can then be screened by exposure to a same common modifying agent to determine the interaction between the modifying agent and the different receptor materials.

Detectors

The term "detector" is used herein to denote any instrument which can be used to ascertain a property of the modifying agent in the stream of liquid carrier (including, as noted above, a property of part of the modifying agent and a property of a substance which is produced by the interaction of the modifying agent and the receptor). Hence, the detector can be a flow detector as known in the chromatographic arts. Preferably the detector operates without removing anything from the stream (i.e. is non-destructive). Such detectors measure, for example, (i) the adsorption by the liquid stream of radiation whose wavelength is absorbed to by the modifier but not by the liquid carrier, (ii) the fluorescence of the stream, or (iii) the refractory index of the stream. The detector often makes a series of measurements at spaced intervals of time, and (via transducers and amplifiers) produces a concentration profile from which, for example, the total quantity of the modifying agent in the stream and the peak value of the concentration of the modifying agent can be determined. The detector may measure the presence or absence of a particular ingredient, and may produce results in the form of a graph having a maximum or a minimum, each of which is referred to herein as a "peak". Such detectors are well-known to those skilled in the art. Additional useful information may be available from the shape of the concentration profile. For example the more symmetrical the peak (i.e. the smaller the size of the tail representing material which is extracted from the solid phase by the subsequent stream of liquid carrier), the less reversible the interaction between the modifying agent and the receptor. The center of gravity of the concentration profile (i.e. the time at which half of the total detected amount of the modifying agent has passed through the detector) shows the average retention time of the modifying agent in the test chamber. FIGS. 3, 5, 7 and 8 are typical plots of time against a measured value which is directly proportional to the amount of the modifying agent in the stream leaving the test or reference chamber.

Test Chambers

The test chamber can be any structure which will contain the solid phase so that the stream of liquid carrier can be passed over it. Hence, the test chamber typically has at least one inlet and at least one outlet. The volume of test chamber will often be from 0.01 to 50 mL, preferably 0.2 to 5 mL. The test chamber will often be cylindrical, with a diameter of 0.1 to 30 mm, preferably 1 to 8 mm, and a length of 1 to 150 mm, preferably 3 to 30 mm. However, chambers of other shapes can be used, typically with the same cross-sectional areas and lengths. The solid phase can be retained within the test chamber in any way. Often the solid phase is packed within the chamber so that the stream of liquid carrier flows through the chamber at a linear velocity of 0.01 to 10, preferably 0.5 to 2, cm/min and/or a flow rate of 0.01 to 50, preferably 0.5 to 5, mL/min. The efficiency of the test chamber, with the solid phase therein, is generally less than 80 theoretical plates, preferably less than 50 theoretical plates, particularly less than 10 theoretical plates, and in many cases is 2–5, for example 3–4, theoretical plates.

Reference Chambers

In some embodiments of the invention, the need to determine absolute amounts of the modifying agent is eliminated by passing a reference sample through a reference chamber. Hence, the reference chamber has at least one inlet and at least one outlet. The reference chamber is free of any substance which interacts with the modifying agent, and in some cases is simply empty. That is, the reference chamber has an essential absence of interferring solid phase media—especially solid phase media that would interfere substantially with the evaluation of the reference section. Hence, the reference chamber can comprise materials that are interactively inert with respect to the test sample, and particularly, with respect to the modifying agent in the test sample. Examination of the stream leaving the reference chamber provides a reference standard from which the proportion of the modifying agent retained in the test chamber can be ascertained. When the streams leaving the test and reference chambers are examined by different detectors, their void volumes are preferably substantially the same (for example, from 0.8 to 1.2 times the arithmetic average of their void volumes). When the liquid stream is split, and the two resulting sub-streams are passed through the test and reference chambers, recombined and examined by the same detector, the void volumes of the loops containing the test and reference chambers can be sufficiently different that the detector can distinguish between the sections which have passed through the different chambers. The sections need not be entirely distinct, provided that the amount of modifying agent in each can be ascertained with sufficient accuracy for the purposes of the invention. For example, the smaller of the void volumes can be 0.5 to 0.8 times the larger of void volumes. The void volume of a chamber is its total volume less the volume occupied by any solid material therein.

Test Procedures

Generally the temperature, pressure, flow rates, sample sizes, and other test conditions are the same in each of the test procedures and the receptor, modifying agent and liquid carrier are the same in each of the test procedures, except that in each test procedure a different member of the library is used. Often all the test procedures are substantially identical except for the use of the different member of the library. However, this is not necessary. For example, the detector can be programmed simply to report that the test was negative if the peak height of the concentration profile is over a particular value; or there can be a feedback loop to change the rate of flow of the liquid carrier in response to the results in earlier tests. In addition, the invention includes the possibility that at least some of the test procedures (i) differ only in the test conditions, or (ii) differ in the test conditions and otherwise differ only in that each test procedure uses a different member of the library, or (iii) use the same conditions in the test procedures and otherwise differ in that more than one of the receptor, modifying agent and liquid carrier are changed (for example, when more than one of the receptor, modifying agent and liquid carrier are selected from libraries, different members are selected from two or three of the libraries).

The flow rate of liquid carrier through the test chamber is generally 1–10, preferably 2–6, especially 3–5, mL/min.

The conditions in the test chamber can be such that the change in the pressure within the test chamber changes, or does not change, the flow rate of liquid carrier. A graph of the flow rate of the liquid carrier against the pressure in the test chamber generally reaches a plateau at a pressure of less than 5000, preferably less than 1000, particular less than 500, especially less than 100, psi.

Description of the Drawings

FIG. 1 is a diagrammatic illustration of an apparatus for injecting a plurality of liquid units into a stream of a liquid carrier, each unit comprising a modifying agent which is one of a library. In FIG. 1, a liquid carrier 10 is stored in reservoir 11. Pump 12 conveys liquid carrier from the reservoir 11 to an injection port 13. Microtiter plate 14 and injection needle 15 are part of a conventional autodilution and sampling robot. Members of the library are retained separately on the microtiter plate 14 and are sequentially removed by the injection needle 15 and diluted with carrier liquid from the reservoir 11 to form units containing one of the members of the library. The units are then transported to the injection port 13, where they are injected sequentially into the stream of liquid carrier. After passing through filter 16, the stream of liquid carrier, carrying the units in distinct sections, is conveyed down line 17.

FIG. 2 is a diagrammatic illustration of a first apparatus for evaluating the interaction between a solid phase comprising a receptor and a library of modifying agent. A stream of liquid carrier is fed to the apparatus through line 17 (for example from apparatus as illustrated in FIG. 1). The stream contains liquid units in distinct sections, and each unit comprises a modifying agent which is one of the library of second materials. The stream passes through a test chamber 22 containing a solid phase comprising the receptor, and then through a detector 24, before being discarded. The test chamber has an inlet for receiving the liquid carrier, and the liquid test sample in the distinct test section thereof, in fluid communication with a an upstream source of the carrier liquid. The test chamber also has an outlet for discharging the carrier liquid after it has passed through the test chamber, the outlet being in fluid communication with a detector 24. The detector 24 ascertains the amount of the modifying agent remaining in the stream.

FIG. 3 is a typical plot of time against the response of the detector 24 in FIG. 2, for a section of the stream containing a modifying agent which is partially adsorbed by the receptor. In FIG. 3 (and in the other Figures showing the response of the detector), there is a base level which represents the response of the detector to the liquid carrier alone (or to the liquid carrier containing a very small amount of modifying agent which results from the extraction of modifying agent which was deposited on the solid phase in earlier test procedures). The amount of modifying agent in the stream can be calculated from the area under the curve, above the base level. The height of the peak and the shape of the curve can also provide other information about the interaction between the modifying agent and the first solid material. If the amount of the modifying agent originally present in the unit is known, then the amount retained in the test chamber can be calculated from a plot of the type shown in FIG. 3.

FIG. 4 is a diagrammatic illustration of a second apparatus for evaluating the interaction between a receptor and a library of modifying agents. This apparatus makes it possible to determine the percentage of the modifying agent retained by the receptor and is not dependent on the amount of modifying agent originally present in the sample. A stream of liquid carrier is fed to the apparatus through a main passageway, such as line 17 (for example from apparatus as illustrated in FIG. 1). The stream contains liquid units in distinct sections and each unit comprises a modifying agent which is one of the library. The main passageway provides fluid communication between a liquid carrier source (e.g., such as reservoir 11 as shown in FIG. 1) and a flow splitter, such that the liquid unit is divided by the valve 41 into first and second substreams. The splitter is illustrated in FIG. 4 as switching valve 41, which itself is in fluid communication with two or more branch passageways. As illustrated, switching valve 41 is in fluid communication with a first loop defined by a first branch passageway providing fluid communication to an inlet of the test chamber 42, the test chamber 42 itself, and second branch passageway providing fluid communication from an outlet of the test chamber 42 to a common exit passageway. Switching valve 41 is also is also in fluid communication to an second loop defined by a third branch passageway providing fluid communication to an inlet of a reference chamber 43, the reference chamber 43 itself, and a fourth branch passageway providing fluid communication from an outlet of the reference chamber 43 to the common exit passageway. As each unit-carrying section of the liquid stream reaches the switching valve 41, the valve passes a first part of the section containing half of the modifying agent through the first loop containing test chamber 42 and a second part of the section containing the other half of the modifying agent through the second loop containing reference chamber 43. The order in which this is done is not important. (That is, for example, the first part of each unit-carrying section could be directed to the reference chamber loop, and the second part of each unit-carrying section could be directed to the test chamber loop. The test chamber 42 contains a solid phase comprising the receptor. The reference chamber 43 is empty or contains a material which does not interact with the modifying agent (that is, does not not interact to a degree having a substantial effect on the comparison). The void volumes of the first and second loops are preferably substantially the same, but can also be different in some embodiments. For example, the void volumes of the loops containing the chambers 42 and 43 can be sufficiently different that, when the first and second sub-streams are recombined, the detector 44 can ascertain, for each section, the amounts of the modifying agent remaining in the parts of the recombined stream which correspond to the first and second sub-streams. Preferably, the first and second parts of the stream return sequentially from the chambers 42 and 43 respectively to the valve 41 and are recombined in a common exit passageway to form a common exit carrier stream, and are then passed sequentially through a detector 44, before being discarded. The detector 44 is in fluid communication with the common exit passageway and can be used to ascertain the amounts of the modifying agent remaining in the first and second parts of the stream respectively.

Figure 5:
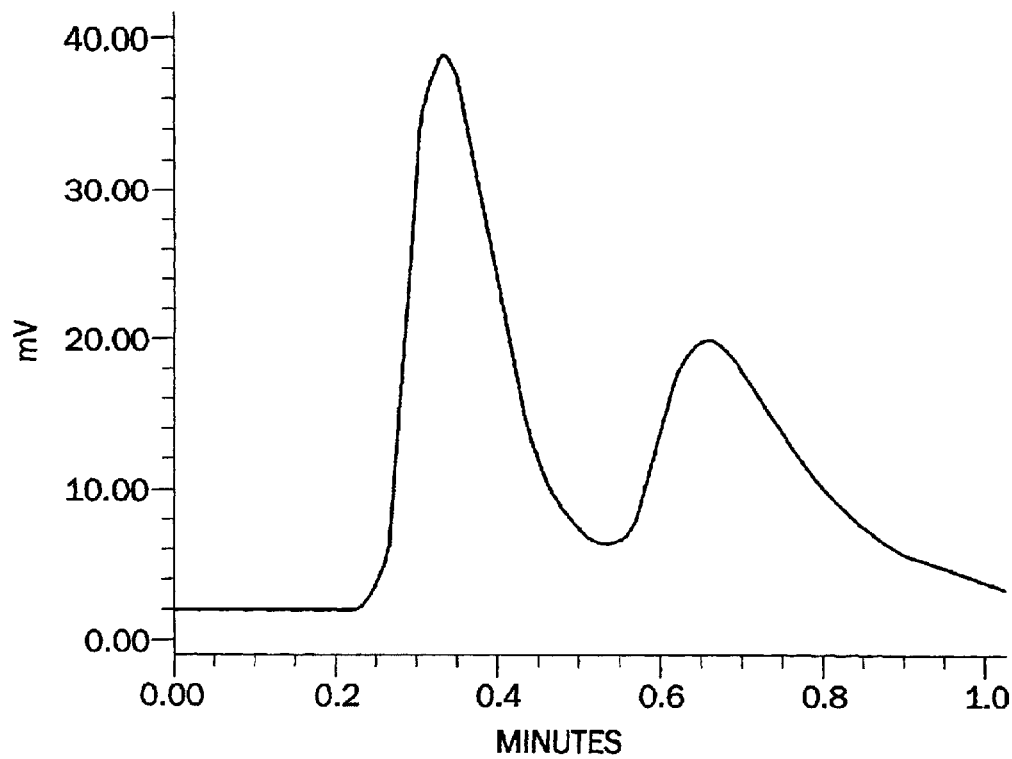

FIG. 5 is a typical plot of time against the concentration of the modifying agent, as measured by the detector 44 in FIG. 4, for a section of the stream containing a modifying agent which is partially adsorbed by the receptor. In this plot, the first curve, containing the sharper and higher peak, is for the modifying agent which passed through the reference chamber, and the second curve, containing the broader and lower peak, is for the modifying agent which passed through the test chamber. If the area under the first curve is A5$a$, and the area under the second curve is A5$b$, the percentage of the modifying agent retained in the test chamber is (A5$a$–A5$b$)/A5$a$. The height of the peak and the shape of the second curve can also provide other information about the interaction between the modifying agent and the receptor.

Figure 6:
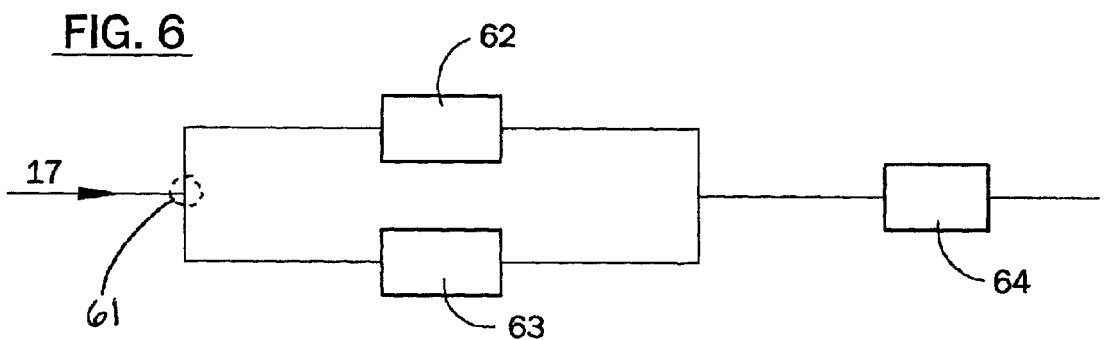

FIG. 6 is a diagrammatic illustration of a third apparatus for evaluating the interaction between a receptor and a library of modifying agents. Like the apparatus shown in FIG. 4, this apparatus makes it possible to determine the percentage of the modifying agent retained in the test chamber and is not dependent on the amount of modifying agent originally present in the sample. Furthermore, unlike the apparatus of FIG. 4, the flow splitter is a stream-splitting junction 61 rather than a switching valve (41, FIG. 4). The junction 61 will consistently direct one half of the modifying agent through the test chamber and the other half through the reference chamber. A stream of liquid carrier is fed to the apparatus of FIG. 6 through a main passageway, such as for example line 17 (for example from apparatus as illustrated in FIG. 1). The liquid carrier carries liquid units in distinct sections, and each unit comprises a modifying agent which can be one of the library members. The main passageway provides fluid communication between a liquid carrier source (e.g., such as reservoir 11 as shown in FIG. 1) and a flow splitter, such that the liquid unit is divided by the stream-splitting junction 61 into first and second substreams. Junction 61 is itself is in fluid communication with two or more branch passageways. Specifically, as illustrated, when the liquid stream reaches junction 61, the stream splits into a first sub-stream and a second sub-stream. Junction 61 is in fluid communication with a first loop defined by a first branch passageway providing fluid communication to an inlet of the test chamber 62, the test chamber 62 itself, and second branch passageway providing fluid communication from an outlet of the test chamber 62 to a common exit passageway. Junction 61 is also in fluid communication with a second loop defined by a third branch passageway providing fluid communication to an inlet of a reference chamber 63, the reference chamber 63 itself, and a fourth branch passageway providing fluid communication from an outlet of the reference chamber 63 to the common exit passageway. In operation, the first sub-stream passes through the first loop containing test chamber 62 and the second sub-stream passes through the second loop containing reference chamber 63. The test chamber 62 contains a solid phase comprising the receptor. The reference chamber 63 is empty or contains a material which does not interact with the modifying agent. The first and second sub-streams are recombined after leaving the chambers 62 and 63 respectively, into a common exit passageway in fluid communication with a detector 64. The recombined stream is passed through the detector 64, before being discarded. The void volumes of the loops containing the chambers 62 and 63 can be the same, but are preferably sufficiently different that, when the first and second sub-streams are recombined, the detector 64 can ascertain, for each section, the amounts of the modifying agent remaining in the parts of the recombined stream which correspond to the first and second sub-streams.

Figure 7:
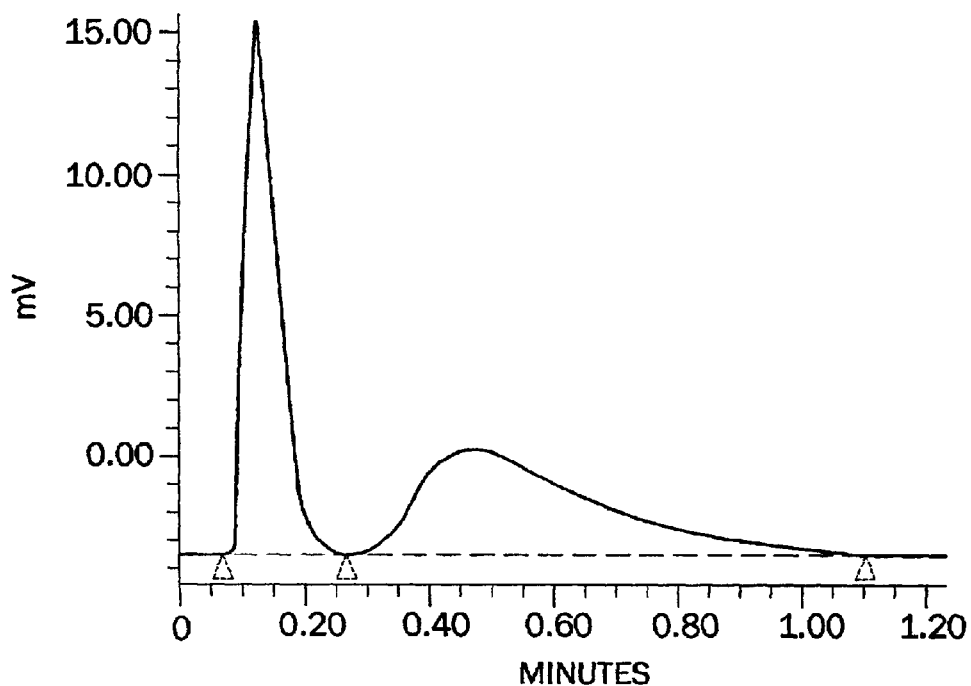

FIG. 7 is a typical plot of time against the concentration of the modifying agent, as measured by the detector 64 in FIG. 6, for a section of the stream containing a liquid sample in which the modifying agent is partially adsorbed by the receptor. In this plot, the first curve, containing the sharper and higher peak, is for the modifying agent remaining in the part of the stream which passed through the empty chamber, and the second curve, containing the broader and lower peak, is for the modifying agent remaining in the part of the stream which passed through the chamber containing the first solid material. In order to ascertain from FIG. 7 the percentage of the modifying agent retained in the test chamber, it is necessary to know the flow splitting ratio between the test chamber and the reference chamber. The flow splitting ratio can be ascertained by replacing the library material by an additive which does not interact with the solid phase in the test chamber.

Figure 8:
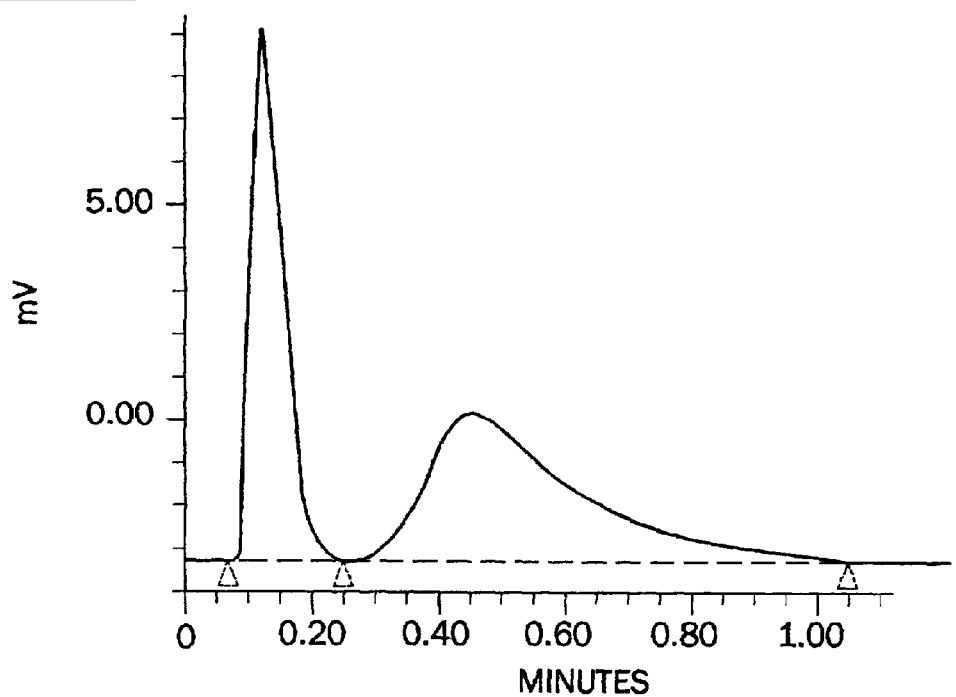

FIG. 8 is a typical plot of the concentration of such an additive, as measured by the detector 64. In this plot, the first curve, containing the sharper and higher peak, is for the additive which passed through the empty chamber, and the second curve, containing the broader and lower peak, is for the additive which passed through the chamber containing the first solid material. The flow splitting ratio (FSR) is the ratio of the area under the first curve to the area under the second curve. If the area under the first curve in FIG. 7 is A7$a$, the area under the second curve in FIG. 7 is A7$b$, the area under the first curve in FIG. 8 is A8$a$, and the area under the second curve in FIG. 8 is A8$b$, the percentage of the modifying agent retained in the test chamber is 100–[100× A7$a$/A7$b$×A8$a$/A8$b$]. The shape of the second curve can also provide information about the rate of interaction between the modifying agent and the first solid material.

Figure 9:
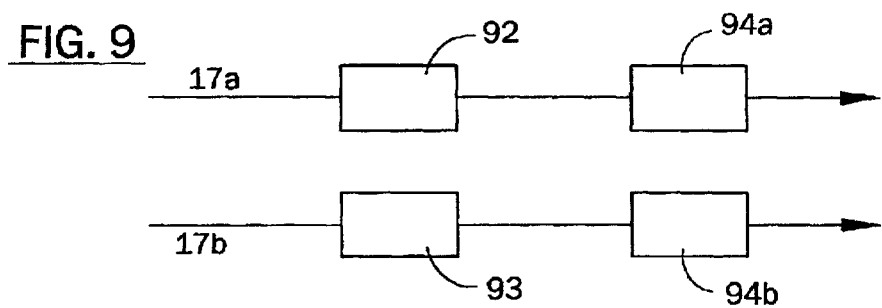

FIG. 9 is a diagrammatic illustration of a fourth apparatus for evaluating the interaction between a receptor and a library of modifying agents. In FIG. 9, a first stream of carrier liquid is fed through line 17$a$ (for example from apparatus as illustrated in FIG. 1). The stream contains liquid samples in distinct sections and each sample comprises a modifying agent which is one of the library. The stream passes through a test chamber 92 which contains a solid phase comprising the receptor, and then through a detector 94$a$, before being discarded. A second stream, identical to the first stream, is fed through line 17$b$ (for example from apparatus as illustrated in FIG. 1), through a reference chamber 93 which is empty or contains a material which does not interact with the modifying agent, and then through a detector 94$b$, before being discarded.

Figure 10:
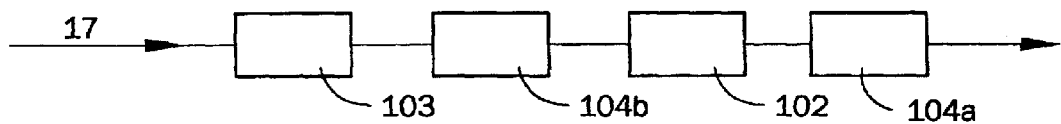

FIG. 10 is a diagrammatic illustration of a fifth apparatus for evaluating the interaction between a receptor and a library of modifying agents. In FIG. 10, a stream of carrier liquid is fed through line 17 (for example from apparatus as illustrated in FIG. 1). The stream contains liquid samples in distinct sections and each sample comprises a modifying agent which is one of the library. The stream passes consecutively through a reference chamber 103 which is empty or contains a material which does not interact with the modifying agent, a first detector 104b, a test chamber 102 which contains a solid phase comprising the receptor, and second detector 104a, before being discarded.

The proportion of modifying agent retained in the test chamber in FIGS. 9 and 10 can be determined in the way described above for FIGS. 4 and 5.

Figure 11:
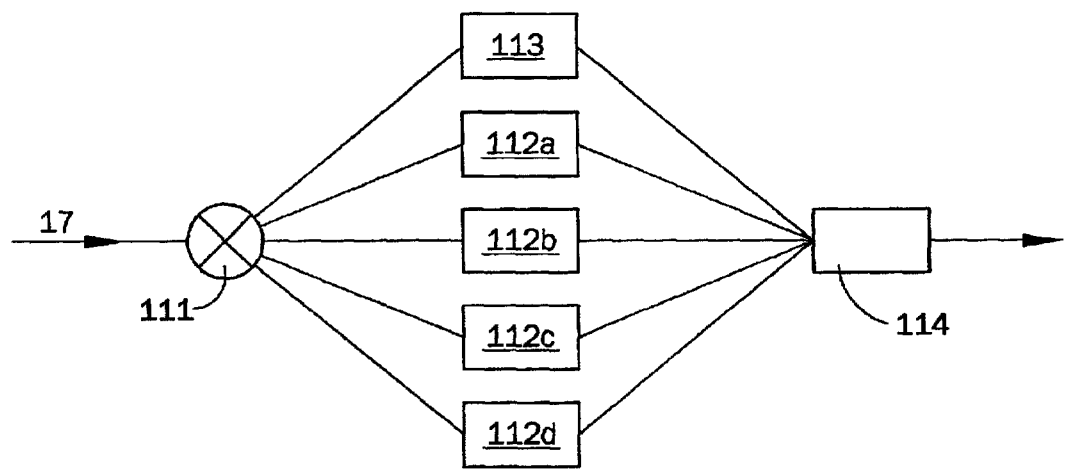

FIG. 11 is a diagrammatic illustration of a sixth apparatus for evaluating the interaction between a receptor and a library of modifying agents. In a stream carrier liquid is fed through line 17 (for example from apparatus as illustrated in FIG. 1). The stream contains liquid samples in distinct sections and each sample comprises a modifying agent which is one of the library. The sample-carrying stream is fed to a valve 111 which sequentially directs successive sub-streams, each sub-stream containing a single sample, to a loop containing a reference chamber 113 and to one of a plurality of loops each containing a test chamber 112a,b,c . . . Four test chambers are shown in FIG. 11, but any appropriate number, for example from 2 to 64, could be used. Each of the test chambers contains a solid phase comprising the receptor. The reference chamber is empty or contains a material which does not interact with the modifying agent. The liquid sub-streams, after passing through the reference or test chamber, are recombined into a single combined stream containing substantially separate evaluation sections corresponding to the samples. The combined stream is passed through a detector 114, which detects the amount of modifying agent in each of the evaluation sections in turn.

The apparatus of the type shown in FIG. 11 can also be used to evaluate the interaction between a modifying agent and a library of receptors. In this case, the liquid samples in the stream are identical, and the solid phase in each of the test chambers comprises one of the library of receptors. In apparatus of the type shown in FIG. 11, the single detector 114 could be replaced by a plurality of detectors, each examining a single sub-stream or a suitable proportion of the sub-streams.

EXAMPLES

The invention as illustrated in the following Examples.

Example 1

Apparatus of the type shown in FIGS. 1 and 4 was used to evaluate the interaction between (i) a copolymer of N-(3-(dimethylamino) propyl) methacrylamide, styrene and acrylic acid, in a molar ratio of 98.3:0.1:0.12, and (ii) a cotton fabric. The cotton fabric was a plain white untreated cotton sheet, about 50 mm wide, rolled tightly and inserted into the column. The pump was a high performance liquid chromatography (HPLC) pump sold by Waters under the tradename Model 515. The injection port was a two-position injection valve sold by Valco under the tradename Model EHMA. The valve was equipped with two 50 microliter injection loops. The multiposition switching valve was a valve sold by Valco under the tradename Model EMTMA-CE.

The liquid carrier was a 1% by weight solution of ammonium acetate in deionized distilled water to which had been added sufficient ammonium hydroxide to bring the pH to 10.5 and 1% by weight of a stock detergent solution. The stock detergent solution was composed of ionized distilled water to which had been added 0.6 g/L of a proprietary linear alkane sulfonate, 0.4 g/L. of a proprietary non-ionic surfactant, 1.25 g/L. of sodium carbonate, 1.1 g/L. of pentasodium triphosphate, 1.0 g/L. sodium chloride and 0.0882 g/L. of calcium chloride dihydrate. The flow rate of the liquid carrier was about 4 mL/min.

The liquid sample contained 2 mg/mL of the copolymer dissolved in the liquid carrier. The time between the injections was 2 minutes.

The test chamber was a stainless steel column having a height of 50 mm and an internal diameter of 7.5 mm, with the cotton fabric tightly rolled to completely fill the column. The reference chamber was a proprietary on-line pre-column HPLC metal filter sold by Valco Instruments. The passageways connected to the first and second chambers were sized to insure that the void volumes of the first and second loops were substantially the same.

The detector was an evaporative light scattering detector sold by Polymer Laboratories under the tradename Model ELSD-1000. The results obtained by the detector are shown in FIG. 5.

Example 2

Apparatus of the type shown in FIGS. 1 and 6 was used to evaluate the interaction between (i) the cotton fabric used in Example 1 and (ii) (a) the copolymer used in Example 1, and (b) a library of 96 different polymers each composed of units derived from three monomers. Details of the polymers in the library are shown in Table 1 below, which gives the proportions by weight of the units derived from each of the three monomers, the first figure being for units derived from 4-acetoyloxymethyl) styrene, the second figure being for units derived from 2-hydroxyethyl methacrylate, and the third figure being for units derived from 2-(dimethylamino) ethyl methacrylate.

The autodilution and sampling robot, the pump, the injection port and the detector were as described in Example 1. The test chamber and the reference chamber were as described in Example 1, but the passageways to and from them were sized so as to insure that, in the combined stream entering the detector, the samples from the respective chambers were substantially separated so that they could be ascertained separately by the detector.

The liquid carrier, and its flow rate, were as in Example 1.

The liquid sample contained about 2 mg/mL of the polymer dissolved in a liquid carrier, and each sample was about 50 microliters. The time between the injections was 3 minutes.

The results obtained by the detector are shown in FIG. 5.

TABLE 1

|   | 1 | 2 | 3 | 4 | 5 | 6 | 7 | 8 | 9 | 10 | 11 | 12 |
|---|---|---|---|---|---|---|---|---|---|----|----|----|
| 1 | 30 | 30 | 30 | 30 | 30 | 30 | 30 | 30 | 30 | 30 | 30 | 30 |
|   | 69 | 64 | 58 | 53 | 47 | 41 | 36 | 30 | 25 | 19 | 13 | 41 |
|   | 1 | 6 | 12 | 18 | 23 | 29 | 34 | 40 | 46 | 51 | 57 | 29 |
| 2 | 25 | 25 | 25 | 25 | 25 | 25 | 25 | 25 | 25 | 25 | 25 | 25 |
|   | 74 | 68 | 62 | 56 | 50 | 44 | 38 | 32 | 26 | 20 | 14 | 44 |
|   | 1 | 7 | 13 | 19 | 25 | 31 | 37 | 43 | 49 | 55 | 61 | 31 |
| 3 | 20 | 20 | 20 | 20 | 20 | 20 | 20 | 20 | 20 | 20 | 20 | 20 |
|   | 79 | 73 | 66 | 60 | 54 | 47 | 41 | 34 | 28 | 22 | 15 | 47 |

TABLE 1-continued

|   | 1 | 2 | 3 | 4 | 5 | 6 | 7 | 8 | 9 | 10 | 11 | 12 |
|---|---|---|---|---|---|---|---|---|---|---|---|---|
| 4 | 1  | 7  | 14 | 20 | 26 | 33 | 39 | 46 | 52 | 58 | 65 | 33 |
|   | 15 | 15 | 15 | 15 | 15 | 15 | 15 | 15 | 15 | 15 | 15 | 15 |
|   | 84 | 77 | 71 | 64 | 57 | 50 | 43 | 37 | 30 | 23 | 16 | 50 |
| 5 | 1  | 8  | 14 | 21 | 28 | 35 | 42 | 48 | 55 | 62 | 69 | 35 |
|   | 10 | 10 | 10 | 10 | 10 | 10 | 10 | 10 | 10 | 10 | 10 | 10 |
|   | 89 | 82 | 75 | 68 | 60 | 53 | 46 | 39 | 32 | 24 | 17 | 53 |
| 6 | 1  | 8  | 15 | 23 | 30 | 37 | 44 | 51 | 59 | 66 | 73 | 37 |
|   | 8  | 8  | 8  | 8  | 8  | 8  | 8  | 8  | 8  | 8  | 8  | 8  |
|   | 92 | 84 | 77 | 69 | 62 | 55 | 47 | 40 | 32 | 25 | 18 | 55 |
| 7 | 1  | 8  | 16 | 23 | 31 | 38 | 45 | 53 | 60 | 68 | 75 | 38 |
|   | 5  | 5  | 5  | 5  | 5  | 5  | 5  | 5  | 5  | 5  | 5  | 5  |
|   | 94 | 86 | 79 | 71 | 64 | 56 | 48 | 41 | 33 | 26 | 18 | 56 |
| 8 | 1  | 9  | 16 | 24 | 31 | 39 | 47 | 54 | 62 | 69 | 77 | 39 |
|   | 3  | 3  | 3  | 3  | 3  | 3  | 3  | 3  | 3  | 3  | 3  | 3  |
|   | 97 | 89 | 81 | 73 | 65 | 58 | 50 | 42 | 34 | 26 | 19 | 58 |
|   | 1  | 9  | 17 | 24 | 32 | 40 | 48 | 56 | 63 | 71 | 79 | 40 |

In order to determine the flow splitting ratio of the apparatus, a sample of poly(N-vinylpyrrolidone), a polymer which does not interact with the cotton fabric, is passed through the apparatus. FIG. 8 shows the results recorded by the detector. The are A3 under the narrow, higher peak, from the stainless-steel filter, was about 43,000. The area A4 under the broad, lower peak, from the first chamber containing the cotton fabric, was about 62,800. Thus the flow splitting ratio was 0.685.

A sample of the copolymer used in Example 1 was then passed through the apparatus. FIG. 7 shows the results recorded by the detector. The area A1 under the Narrow, higher peak, from the stainless-steel filter, was about 65,900. The area A2 under the broader, lower peak, from the first chamber containing the cotton fabric, was about 70,500. The percentage of the copolymer remaining in the liquid stream which had passed through the first chamber was, therefore, about 73%, i.e. (70500/65900)×0.685, and the percentage that had been retained by the cotton fabric was about 27%.

Samples of each of the 96 members of the library were then passed through the and the percentage of each retained by the cotton fabric was calculated. The shown in Table 2 below.

TABLE 2

|   | 1 | 2  | 3  | 4  | 5  | 6  | 7  | 8  | 9  | 10 | 11 | 12 |
|---|---|----|----|----|----|----|----|----|----|----|----|----|
| 1 | 0 | 10 | 18 | 3  | 38 | 40 | 41 | 46 | 59 | 45 | 32 | 0  |
| 2 | 0 | 0  | 23 | 48 | 47 | 46 | 54 | 52 | 58 | 45 | 50 | 0  |
| 3 | 0 | 16 | 13 | 45 | 39 | 41 | 58 | 48 | 56 | 44 | 28 | 0  |
| 4 | 0 | 13 | 9  | 20 | 31 | 36 | 27 | 15 | 32 | 36 | 16 | 4  |
| 5 | 0 | 1  | 5  | 0  | 2  | 16 | 6  | 8  | 19 | 21 | 16 | 19 |
| 6 | 0 | 0  | 0  | 0  | 0  | 0  | 4  | 5  | 7  | 9  | 24 | 0  |
| 7 | 0 | 0  | 0  | 0  | 0  | 0  | 3  | 0  | 15 | 17 | 22 | 46 |
| 8 | 0 | 0  | 8  | 0  | 0  | 0  | 4  | 6  | 5  | 18 | 23 | 0  |

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A method for evaluating the interaction between a receptor comprising natural or artificial mammalian tissue and a modifying agent in the presence of a liquid carrier, the method comprising:

providing the receptor comprising natural or artificial mammalian tissue, and providing the modifying agent, one of the receptor and modifying agent being provided as a member of a combinatorial library having at least four members, conducting at least four test procedures with the receptor, modifying agent and liquid carrier being the same in each of the test procedures except that in each test procedure a different member of the combinatorial library is used, each of the test procedures comprising:

(a) injecting a liquid test sample comprising the modifying agent into a stream of the liquid carrier, the injection being carried out over a limited time so that a distinct test section of the stream contains the test sample, (b) passing the stream of liquid carrier containing the test sample over a solid phase in a test chamber, the solid phase comprising the receptor, and (c) examining the stream of liquid carrier leaving the test chamber to ascertain a variable which reflects the interaction of the modifying agent and the receptor in the presence of the liquid carrier.

2. The method according to claim 1 wherein modifying agent comprises a non-biological polymer.

3. The method according to claim 1 wherein the library is a library of receptors.

4. The method according to claim 1 wherein the library is a library of receptors, each of the members of the library comprising a different natural or artificial mammalian tissue.

5. The method according to claim 1 wherein the library is a library of receptors, each of the members of the libraries comprising a same common natural or artificial mammalian tissue that has been pretreated with a different non-biological polymer.

6. The method according to claim 1 wherein the library is a library of modifying agents.

7. The method according to claim 1 wherein the library is a library of modifying agents, each of the at least four members of the library comprising a therapeutic agent or a diagnostic agent.

8. The method according to claim 1 wherein the library is a library of modifying agents, each of the at least four members of the library comprising a different therapeutic agent or a different diagnostic agent.

9. A method for evaluating the interaction between a receptor comprising natural or artificial mammalian tissue and a modifying agent comprising a non-biological polymer in the presence of a liquid carrier, the method comprising:

providing the receptor comprising natural or artificial mammalian tissue, and providing the modifying agent comprising a non-biological polymer, the modifying agent being provided as a member of a combinatorial library having at least four members, each of the at least four members of the library comprising a different non-biological polymer, conducting at least four test procedures with the receptor and liquid carrier being the same in each of the test procedures, and with a different member of the combinatorial library being used in each of the at least four test procedures, each of the test procedures comprising:

(a) injecting a liquid test sample comprising the modifying agent into a stream of the liquid carrier, the injection being carried out over a limited time so that a distinct test section of the stream contains the test sample, (b) passing the stream of liquid carrier containing the test sample over a solid phase in a test chamber, the solid phase comprising the receptor, and (c) examining the stream of liquid carrier leaving the test chamber to ascertain a variable which reflects the interaction of the modifying agent and the receptor in the presence of the liquid carrier.

10. The method according to claim 9 wherein each of the at least four members of the library of modifying agents further comprises a therapeutic agent or a diagnostic agent.

11. The method according to claim 9 wherein each of the at least four members of the library of modifying agents comprises a different non-biological polymer and either a same common therapeutic agent or a same common diagnostic agent.

12. The method according to claim 1 or 9 wherein the liquid carrier is water or an aqueous solution.

13. The method according to claim 1 or 9 wherein the receptor comprises natural mammalian tissue.

14. The method according to claim 1 or 9 wherein the receptor comprises artificial mammalian tissue.

15. The method according to claim 1 or 9 further comprising:
(d) using the results from the steps (c) of the test procedures to select at least one member of the library for further testing; and
(e) subjecting the member or members of the library selected in step (d) to further testing.

16. The method according to claim 1 or 9 wherein the at least four test procedures are conducted in parallel.

17. The method according to claim 1 or 9 wherein in each of the test procedures, the efficiency of the test chamber is less than 50 theoretical plates.

18. The method according to claim 1 or 9 wherein in each of the test procedures, the efficiency of the test chamber is less than 10 theoretical plates.

19. The method according to claim 1 or 9 wherein in each of the test procedures, the test sample comprises an initial quantity of the modifying agent, and at least 10% of the initial quantity of the modifying agent is irreversibly retained on the solid phase in the test chamber under test conditions of the procedures.

20. The method according to claim 1 or 9 wherein in each of the test procedures, the test sample comprises an initial quantity of the modifying agent, and 30% to 50% of the initial quantity of the modifying agent is irreversibly retained on the solid phase in the test chamber under test conditions of the procedures.

21. The method according to claim 1 or 9 wherein in each of the test procedures, the test sample comprises an initial quantity of the modifying agent, a percentage of the initial quantity of the modifying agent is irreversibly retained on the solid phase in the test chamber under test conditions of the procedures, and the difference between the lowest and highest percentages of the initial quantity of modifying agent retained in the test chamber is at least 10% as compared between the at least four test procedures.

22. The method according to claim 1 or 9 wherein in each of the test procedures, the receptor is not saturated by the modifying agent.

23. The method according to claim 1 or 9 wherein in each of the test procedures, a plot of time against concentration of the modifying agent in the stream of liquid carrier leaving the test chamber has only a single peak, with the slope of the plot being positive at all points on one side of the peak and negative at all points after the peak.

24. The method according to claim 1 or 9 wherein the receptor comprises at least 50% by weight of particles having an aspect ratio of at least 2 and at least one dimension which is greater than 100 micron.

25. The method according to claim 1 or 9 wherein in each of the test procedures, the test sample comprises an initial quantity of the modifying agent and step (c) consists essentially of ascertaining the proportion of the initial quantity which remains in the test section.

26. The method according to claim 1 or 9 wherein in each of the test procedures, step (c) comprises examining the stream of liquid carrier leaving the test chamber to ascertain a property of the modifying agent which remains in a distinct evaluation section of the stream corresponding to the test section, and the test procedure further comprises:
(d) injecting a liquid reference sample into a stream of the liquid carrier, the composition of the second sample being substantially identical to the composition of the test sample, and the injection being carried out over a limited time so that only a distinct reference section of the stream contains the reference sample,
(e) passing the stream of liquid carrier containing the reference sample through a reference chamber which is free of any substance which interacts with the modifying agent,
(f) examining the stream of liquid carrier leaving the reference chamber to ascertain a property of the modifying agent remaining in the stream, and
(g) comparing the results obtained in steps (c) and (f) to evaluate the interaction between the receptor and the modifying agent.

27. The method according to claim 26 wherein each of steps (c) and (f) comprises passing the stream of liquid carrier through a detector which measures a property which depends on the concentration of the modifying agent, the measurement being carried out without removing anything from the stream and at intervals which make it possible to ascertain the amount of the modifying agent which remains in the stream.

28. The method according to claim 26 wherein in each of the test procedures comprising steps (d) to (g), the liquid stream containing the test section and the liquid stream containing the reference section are obtained by
injecting into the stream of liquid carrier a liquid unit whose composition is the same as the composition of the test and reference samples and whose size is equal to the sum of the sizes of the test and reference samples, the injection being carried out over a limited time so that only a distinct section of the liquid stream contains the liquid unit, and
splitting the liquid stream containing the liquid unit into a first sub-stream which passes through the test chamber and includes the test section and a second sub-stream which passes through the reference chamber and includes the reference section.

29. The method according to claim 28 wherein the liquid stream containing the liquid unit is split into the first and second sub-streams by a flow-splitting junction.

30. The method according to claim 28 wherein the liquid stream containing the liquid unit is split into the first and second sub-streams by a switching valve.

31. The method according to claim 26 wherein in each of the test procedures comprising steps (d) to (g), the liquid stream containing the test section and the liquid stream containing the reference section are obtained by
injecting the liquid test sample into a first stream of the liquid carrier, the first stream being contained in a first line in fluid communication with the test chamber so that the first stream containing the test section passes through the test chamber,
injecting the reference sample into a second stream of the liquid carrier, the second stream being contained in a second line in fluid communication with the reference chamber so that the second stream containing the reference section passes through the reference chamber.

* * * * *